(12) United States Patent
Jeong et al.

(10) Patent No.: US 10,511,133 B2
(45) Date of Patent: Dec. 17, 2019

(54) DEVICE FOR GENERATING LINEARLY POLARIZED ULTRA-SHORT TERAHERTZ WAVE

(71) Applicant: Korea Atomic Energy Research Institute, Daejeon (KR)

(72) Inventors: Young Uk Jeong, Daejeon (KR); Boris Gudkov, Daejeon (KR); Nikolay Vinokurov, Daejeon (KR); Ki Tae Lee, Daejeon (KR); Seong Hee Park, Daejeon (KR); Kyuha Jang, Daejeon (KR); Jeong Sang Jo, Busan (KR)

(73) Assignee: Korea Atomic Energy Research Institute, Daejeon (KR)

( * ) Notice: Subject to any disclaimer, the term of this patent is extended or adjusted under 35 U.S.C. 154(b) by 58 days.

(21) Appl. No.: 15/750,668

(22) PCT Filed: Aug. 11, 2016

(86) PCT No.: PCT/KR2016/008851
§ 371 (c)(1),
(2) Date: Feb. 6, 2018

(87) PCT Pub. No.: WO2017/026819
PCT Pub. Date: Feb. 16, 2017

(65) Prior Publication Data
US 2019/0190223 A1    Jun. 20, 2019

(30) Foreign Application Priority Data
Aug. 12, 2015 (KR) .................. 10-2015-0113694

(51) Int. Cl.
*H01S 1/00* (2006.01)
*H01J 63/02* (2006.01)
*G01N 21/3581* (2014.01)

(52) U.S. Cl.
CPC .............. *H01S 1/005* (2013.01); *H01J 63/02* (2013.01); *G01N 21/3581* (2013.01)

(58) Field of Classification Search
CPC ....... H01S 1/005; G01N 21/3581; H01J 63/02
(Continued)

(56) References Cited

U.S. PATENT DOCUMENTS

| 9,337,603 B2 * | 5/2016 | Vinokurov ............. H01J 25/00 |
| 2005/0018298 A1 | 1/2005 | Trotz et al. |

(Continued)

FOREIGN PATENT DOCUMENTS

| KR | 1020050024303 A | 3/2005 |
| KR | 1020090056764 A | 6/2009 |

(Continued)

OTHER PUBLICATIONS

Chul et al.; "Terahertz Wave Generation Technology—Pulsed THz Light Source Technology"; Optics and Technology; 2010; pp. 23-29; vol. 14:1; English-language Abstract.

(Continued)

*Primary Examiner* — Nicole M Ippolito
(74) *Attorney, Agent, or Firm* — The Webb Law Firm

(57) ABSTRACT

Provided is a linearly polarized ultra-short terahertz wave generating device which has a parabolic barrel mirror installed at one side of a multiple thin film, to generate an ultra-short terahertz wave having single linear-polarized light and uniformly formed output distribution.

12 Claims, 4 Drawing Sheets

(58) Field of Classification Search
USPC .......................................... 250/493.1, 504 R
See application file for complete search history.

(56) References Cited

U.S. PATENT DOCUMENTS

| | | | |
|---|---|---|---|
| 2006/0214176 A1* | 9/2006 | Ouchi | B82Y 20/00 |
| | | | 257/98 |
| 2008/0192792 A1* | 8/2008 | Korenblit | H01S 1/02 |
| | | | 372/73 |
| 2011/0193638 A1 | 8/2011 | Balk et al. | |
| 2016/0233379 A1* | 8/2016 | Qin | H01L 29/42316 |

FOREIGN PATENT DOCUMENTS

| | | |
|---|---|---|
| KR | 1020110092551 A | 8/2011 |
| KR | 1020130091203 A | 8/2013 |
| KR | 101337545 B1 | 12/2013 |

OTHER PUBLICATIONS

Hyuk et al.; "Generation and Application of Terahertz Electromagnetic Wave"; Physics and Advanced Technology; 2003; pp. 34-38; English-language Abstract.

* cited by examiner

DEVICE FOR GENERATING LINEARLY POLARIZED ULTRA-SHORT TERAHERTZ WAVE

CROSS-REFERENCE TO RELATED APPLICATIONS

This application is the United States national phase of International Application No. PCT/KR2016/008851 filed Aug. 11, 2016, and claims priority to Korean Patent Application No. 10-2015-0113694 filed Aug. 12, 2015, the disclosures of which are hereby incorporated in their entirety by reference.

TECHNICAL FIELD

The present invention relates to a device for generating a linearly polarized ultra-short terahertz wave, and more particularly, to a device for generating an ultra-short terahertz wave by coherent radiation generated upon passing through a metallic thin foil pile in which ultra-short electron bunches of a relativistic speed having a pulse duration of picosecond ($10^{-12}$ second) or less.

The terahertz (THz) wave refers to an electromagnetic wave in an intermediate band of an infrared light and a microwave, and has transparency to be used for a non-destructive test of an object, or the like. In particular, the terahertz wave may penetrate a variety of non-conductive materials such as fiber and plastic, and as a result, has been used in fields of security screening or the like as disclosed in Korean Patent Laid-Open Publication NO. 10-2005-0024303 ("THz Imaging System and Method", Mar. 10, 2005). In addition, the terahertz wave has transparency but does not have high photon energy enough to damage a biological tissue or a DNA unlike the X-rays, such that it has high biological safety over the X-rays. As a result, research and development to further broaden the application range of the terahertz wave in fields of medical diagnostics, biological material analysis, communications, or the like have been actively conducted. As such, the terahertz wave has both of the transparency and the safety, and therefore may be used for various fields, whereas since it is difficult to develop a terahertz wave source having a powerful output, the terahertz wave is limited in utilization. Accordingly, various research and developments for making a powerful terahertz source have been conducted.

As the representative method for generating the terahertz wave well known, there are photoconductive antenna, optical rectification, surface-field semiconductor, and so on. The photoconductivity means that a current flow by an electron-hole pair phenomenon generated when light is irradiated on materials having a direct bandgap. Here, the photoconductive antenna generates a terahertz electromagnetic wave using the above characteristics and a short carrier lifetime of a semiconductor medium. The optical rectification utilizes nonlinear optical characteristics generated by strong light and uses a time-dependent polarization phenomenon generated when an optical signal source is accepted. Here, the optical rectification uses a principle of radiating a terahertz electromagnetic wave by accelerating electrons inside a medium by a time-dependent electric field for a very short time which is generated when an ultra-short laser pulse polarized in a photoconductive medium is focused by a lens and incident. On the other hand, a phenomenon of generating a terahertz wave when a laser is irradiated on a pure semiconductor surface to which bias is not applied is observed. This phenomenon is that a terahertz wave is radiated by a dipole generated by an intrinsic surface depletion field present on a semiconductor and a difference (photo-Dember effect) in a diffusion speed between electrons and holes. The content is well described in "Generation and Application of Terahertz Electromagnetic Wave" (Son Ju Hyuk, Kang Chul, Physics and Advanced Technology, pp. 34-38, June 2003), "Terahertz Wave Generation Technology—Pulsed THz Light Source Technology" (Kang Chul, Jung Chang Su, Ki Chul Sik, Optics and Technology Vol. 14, NO. 1, pp. 23-29, January 2010), or the like.

On the other hand, a method for generating an ultra-short terahertz pulse using a transition radiation is also known well. The transition radiation is a radiation generated when an electron beam of a relativistic speed passes through an interface between two materials with different refractive indices, and generally, mainly uses a thin metal foil (conducting foil) as the interface. At this time, if the length of the electron beam pulse used is sufficiently short, a powerful pulse electromagnetic wave can be generated by the coherent effect. Using this method, large-scale electron accelerator facilities have generated an ultra-short terahertz pulse of 100 MW.

However, this method still has a limitation in that the generation efficiency is about 100-10,000 times less than that in other electromagnetic wave spectral bands such as visible and infrared light, and microwave. The existing terahertz generation technology using the transition radiation uses one sheet of conducting foil and needs to increase the number of electrons in the incident electron beam to increase the output power of the terahertz wave. Increasing the number of charges of the electron beam is limited by several physical limitations such as performance and space charge of the electron accelerator, and therefore the existing transition radiation has a limitation in further increasing the output power of the terahertz wave.

BACKGROUND ART

In order to increase the output power with respect to the predetermined number of charges by improving the above-mentioned problems, Korean Patent No. 1337545 ("Ultra-short Terahertz Pulse Generator Having Multiple Foils", Nov. 29, 2013 hereinafter referred to as related patent) filed and registered by the present applicant has been disclosed.

The configuration of the device for generating an ultra-short terahertz wave disclosed in the related patent will be briefly described as follows. Unlike the case where a single conducting foil is used in the related art, in the related patent, multiple conducting foils are arranged in parallel at a predetermined interval. At this time, the diameter of the conducting foils is gradually reduced so that the overall shape of the conducting foils becomes conical. If the ultra-short electron beam bunch of the relativistic speed passes through the conducting foils laid in layers, the electromagnetic waves spreading in a concentric circle are generated in the spaces between the respective conducting foils. Thus, the electromagnetic waves generated between the plies of the respective conducting foils are joined at the ends of the conducting foil piles having the conical structure and radiated to a free space in a conical wavefront, and the polarization of the radiated wave is directed to a central part. FIG. 1 is a simplified configuration diagram of a device for generating an ultra-short terahertz wave including conical multiple foils disclosed in the related patent. As shown in FIG. 1, when an electron beam traveling direction is a z direction, the wavefront of the radiated terahertz wave forms a cone.

The apparatus according to the related patent has a great effect of realizing the generation of a terahertz wave of more than tens of times stronger than that of the device of generating a coherent transition radiation using a single foil. That is, the above related patent is a technique that has a great effect to solve the above-mentioned problem of increasing the power of the existing terahertz source. However, as described above, the terahertz wave generated by the related patent has a donut-shaped wave form in which the wavefront is a conical shape, and no output is in the center of the wave. As a result, there is a limit in applying the related patent in the case of applications which wants a uniform distribution or linear polarization.

RELATED ART DOCUMENT

[Patent Document]
1. Korean Patent Laid-Open Publication NO. 10-2005-0024303 ("Terahertz Imaging System and Method", Mar. 10, 2005)
2. Korean Patent No. 1337545 ("Ultra-short Terahertz Pulse Generator Having Multiple Foils", Nov. 29, 2013)

Non-Patent Document

1. "Generation and Application of Terahertz Electromagnetic Wave" (Son Ju Hyuk, Kang Chul, Physics and Advanced Technology, pp. 34-38, June 2003)
2. "Terahertz Wave Generation Technology—Pulsed THz Light Source Technology" (Kang Chul, Jung Chang Su, Ki Chul Sik, Optics and Technology Vol. 14, NO. 1, pp. 23-29, January 2010)

DISCLOSURE

Technical Problem

An object of the present invention is to provide a device for generating linearly polarized ultra-short terahertz wave, which has a parabolic barrel mirror installed at one side of a multiple thin film, to generate an ultra-short terahertz wave having linear polarization and uniformly formed output distribution.

Technical Solution

In one general aspect, a device for generating a linearly polarized ultra-short terahertz wave, includes: a parabolic mirror barrel 110 configured to extend in one direction, and have a parabolic mirror 115 concaved on an upper surface thereof, an end surface of the parabolic mirror 115 perpendicular to the extending direction forming a parabola; a plurality of thin films 120 configured to be arranged on the parabolic mirror 115 in the extending direction of the parabolic mirror barrel 110 and have at least some areas thereof disposed to overlap each other; and an electron accelerator 130 to generate an electron beam passing through the plurality of thin films 120, and if the electron beam passes through the plurality of thin films 120 and spacing spaces, an ultra-short terahertz wave is generated between the spacing spaces.

If the electron beam passes through the thin film 120, the ultra-short terahertz wave is radially wave-guided in the direction perpendicular to the extending direction in the spacing space.

A traveling path of the electron beam is through a central line of the parabola formed by the surface of the parabolic mirror 115.

The terahertz wave traveled downward from a position through which the electron beam passes may be reflected on the parabolic mirror 115 to be traveled in parallel upward.

An upper edge of the thin film 120 may be formed in a straight line, and heights of the plurality of thin films 120 may be sequentially increased or decreased toward the extending direction. The heights of the plurality of thin films 120 may be linearly increased or decreased.

Wavefronts of the ultra-short terahertz waves radiated from the edge of the spacing space may be combined with each other, and the ultra-short terahertz waves may be radiated while maintaining a planar wavefront in the free space.

The plurality of thin films 120 may be disposed to be parallel with each other so that an interval between the spacing spaces is constant. The electron beam may be traveled in a direction perpendicular to the thin film 120.

The spacing space may vacuum or may be filled with a dielectric material.

The thin film 120 may be made of a metal material.

The electron beam may be formed in a pulse duration of several picoseconds or less.

Advantageous Effects

According to the present invention, the principle of generating coherent radiation of the terahertz spectral region while passing the electron beam of the relativistic speed through the multiple thin conductive foils instead of the single foil, thereby generating the terahertz wave of more than tens of times stronger than the device for generating a coherent transition radiation using the single foil. According to the technology using the existing single foil, the number of electrons in the electron beam incident on the conducting foil should be increased in order to increase the output power, and the performance of the electron accelerator should be improved in order to increase the number of electrons. However, according to the present invention, the electron accelerator having the same performance is used but the small-sized multiple foil structure is used, thereby realizing the increase in power without almost consuming costs.

First of all, according to the present invention, the terahertz wave which has linear polarization, has the uniform output distribution by installing the parabolic barrel mirror at one side of the multiple thin films. In the case of the existing technology of using the plurality of circular conducting foils disposed in the conical shape, the terahertz radiation is conic wave having the donut-shaped wave form in which the wavefront is the conical shape, and no output is in the center of the wave. Therefore, the existing technology is difficult to apply when the uniform distribution or linear polarization are required and thus has a limit of the application range. However, according to the present invention, as described above, the terahertz wave having the uniform output distribution and linear polarization is generated and therefore the limit problems of applications can be solved.

In other words, according to the present invention, the device for generating a high-power ultra-short terahertz wave can be implemented even in the small-sized apparatus by reducing the capacity and cost of the expensive electron accelerator, and also has excellent characteristics to allow the generated terahertz wave to have the uniform output distribution and linear polarization, such that the device can be used for a greater variety of fields than the related art. In particular, the device for generating a high-power ultra-short terahertz wave is expected to be used in advanced research and security inspection technology.

DETAILED DESCRIPTION OF MAIN ELEMENTS

110: Parabolic mirror barrel 115: Parabolic mirror
120: Thin films 130: Electron accelerator

BEST MODE

Hereinafter, a device for generating a linearly polarized ultra-short terahertz wave according to an exemplary embodiment of the present invention having the above-mentioned configuration will be described in detail with reference to the accompanying drawings.

Figure 2:
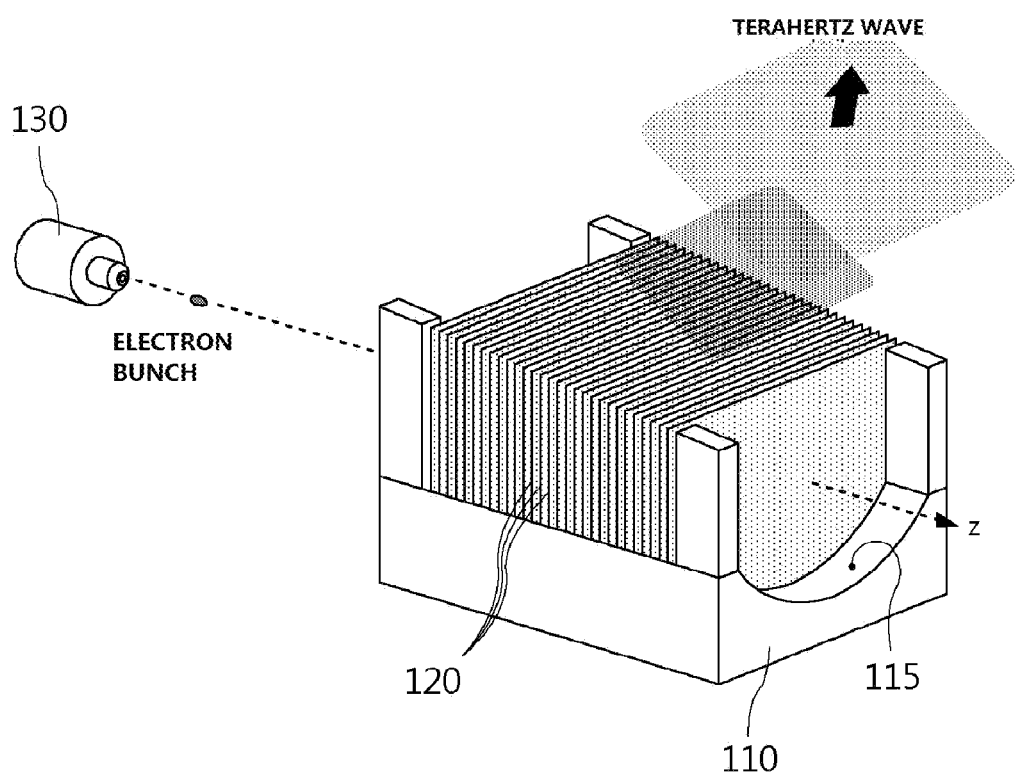
FIG. 2 is a perspective view of a device for generating a linearly polarized ultra-short terahertz wave according to the present invention.
Figure 3:
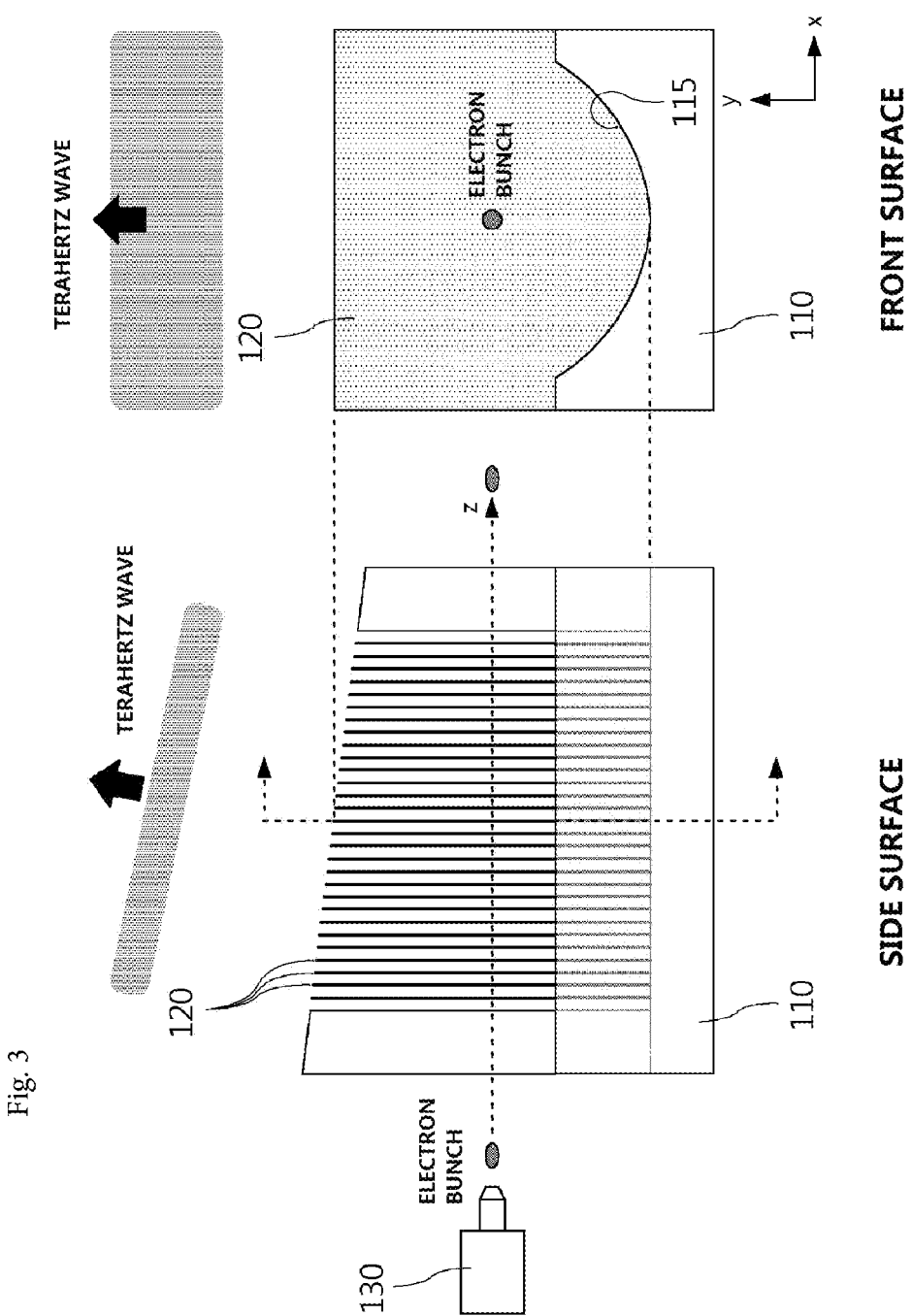
FIG. 3 is a side view and a front view of the device for generating a linearly polarized ultra-short terahertz wave according to the present invention.
Figure 4:
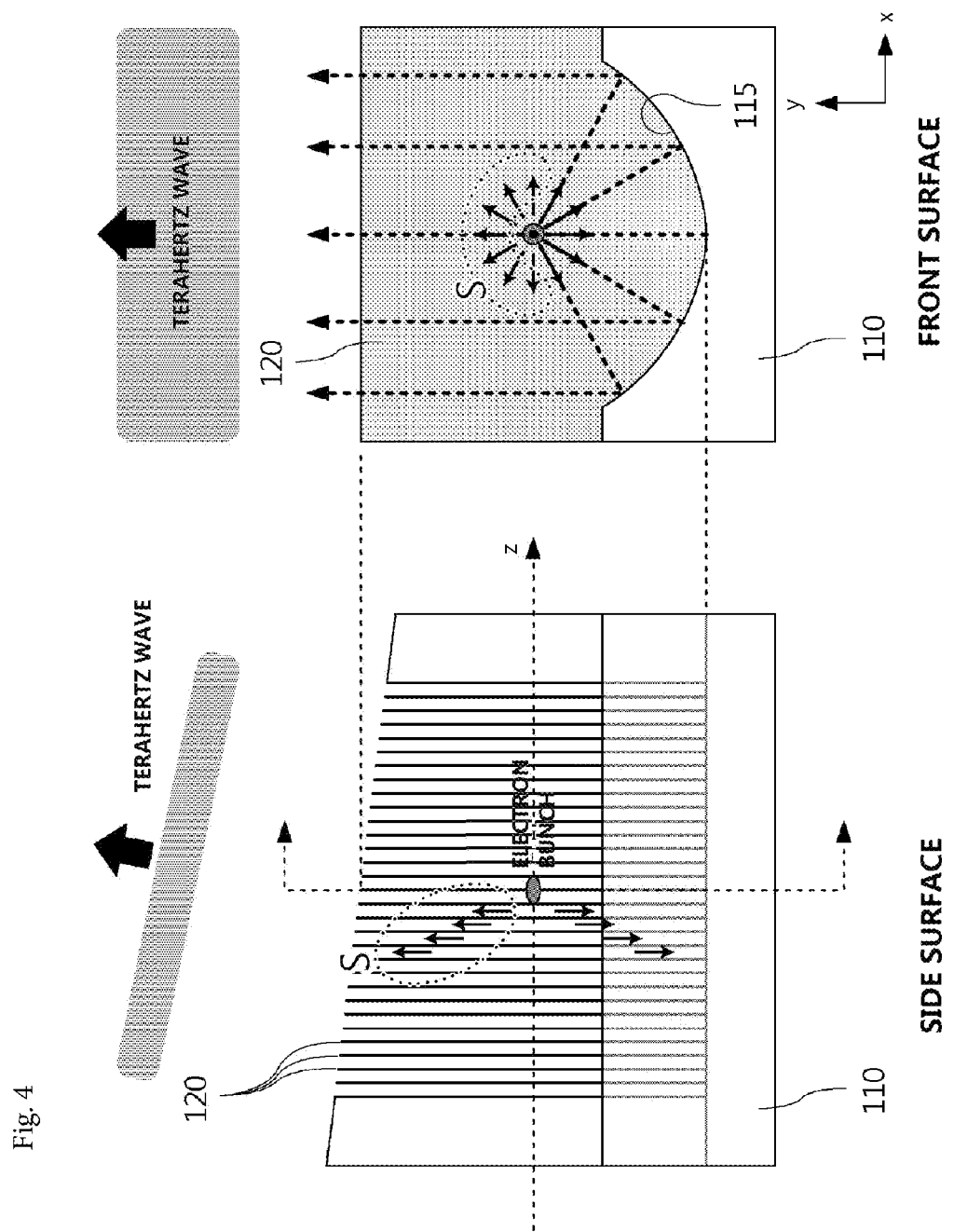
FIG. 4 is a view illustrating a principle of a device for generating a linearly polarized ultra-short terahertz wave according to the present invention.

FIG. 2 is a perspective view of a device for generating a linearly polarized ultra-short terahertz wave according to the present invention and FIG. 3 is a side view and a front view of the device for generating a linearly polarized ultra-short terahertz wave according to the present invention. FIG. 4 is a view illustrating in more detail a principle of a device for generating a linearly polarized ultra-short terahertz wave according to the present invention. As illustrated, the device for generating a linearly polarized ultra-short terahertz wave according to the present invention includes a parabolic mirror barrel 110, a plurality of thin films 120, and an electron accelerator 130. As described above, the basic principle of the present invention is that coherent radiation having a terahertz bandwidth is wave-guided while an electron beam radiated from the electron accelerator passes through the thin films. At this time, according to the present invention, the parabolic mirror barrel has been adopted to generate a linearly polarized terahertz wave whose output distribution is uniformly formed. Hereinafter, each component will be described first with reference to FIGS. 2 and 3, and then the principle of generating the terahertz wave according to the present invention will be described in more detail with reference to FIG. 4.

The parabolic mirror barrel 110 is formed to extend in one direction, and has a parabolic mirror 115 concaved on an upper surface thereof, in which an end surface of the parabolic mirror 115 perpendicular to the extending direction forms a parabola. In FIGS. 2 to 4, the extending direction of the parabolic mirror barrel 110 is represented in a z direction.

The thin films 120 is arranged on the parabolic mirror 115 in the extending direction of the parabolic mirror barrel 110 (i.e., in the z direction in FIGS. 2 to 4), and is arranged so that at least some areas thereof overlap each other. Herein, the term "overlapped" means that the thin films are disposed so as to overlap each other when viewed from the extending direction (i.e., the z direction in FIGS. 2 to 4) of the parabolic mirror barrel 110. Here, the 'at least some areas overlap each other' means that the entire area may overlap each other or some areas may overlap each other. Describing in more detail the thin films 120, as described above, since the thin films 120 is used as an interface for generating a coherent radiation by allowing the electron beam to pass therethrough, the thin films 120 is preferably made of a metal material to reduce the waveguide loss of the generated radiation but is not necessarily made of the metal material. In addition, the thin films 120 may be formed in a thin plate having a thickness of several tens of micrometers or less. In order to neglect an energy loss of the electron beam and extension of a pulse duration due to multiple scattering, the thinner the thin films 120, the more preferable it is.

The electron accelerator 130 generates the electron beam that is traveled along the extending direction of the parabolic mirror barrel 110 to pass through the plurality of thin films 120. The electron accelerator 130 generates an electron beam having a high kinetic energy by accelerating electrons using an electrostatic field, a radio frequency electric field in an acceleration cavity, or the like. In the exemplary embodiment of the present invention, as illustrated, the ultra-short electron bunch is travelling to the z direction. That is, the electron bunch has relativistic speed which has kinetic energy of about one million electron volts (MeV) or more, and in order to effectively generate a coherent radiation in a terahertz band, the electron bunch has a pulse duration of several picoseconds or less.

In the device for generating a linearly polarized ultra-short terahertz wave of the present invention configured as described above, spacing spaces are formed between some areas where the plurality of the thin films 120 overlap each other, and the ultra-short terahertz wave is generated between the spacing space if the electron beams passes through the plurality of thin films 120 and spacing spaces. Describing in more detail, if the electron beam passes through the thin film 120, the radiation in the terahertz spectral band is radiated. The radiation is wave-guided and spread between the thin films 120 (i.e., the spacing space) in a form of a transverse electromagnetic (TEM) wave, that is, in a form in which a direction of an electric vector and a direction of a magnetic vector are perpendicular to each other and are perpendicular to a propagation direction. Here, the electromagnetic wave wave-guided and spread in the TEM wave form is not dispersed and therefore the radiation maintains the ultra-short pulse duration. That is, if the electron beam passes through the thin film 120, the electron beam is formed so that the ultra-short terahertz wave is radially wave-guided in the direction perpendicular to the extending direction in the spacing space.

At this time, an interval between the spacing spaces formed between the plurality of thin films 120 is preferably constant, but may be different if necessary. However, it is preferable that the interval between the spacing spaces is similar to or shorter than the length of the electron bunch. In addition, it is preferable that the plurality of thin films 120 are arranged parallel to each other so that the ultra-short terahertz wave wave-guided in the spacing space is traveled in parallel. By the above arrangement, the electron beam is traveled in a direction perpendicular to the thin films 120.

Further, in order to allow the electron beam and the terahertz wave to be wave-guided well, the spacing space is preferably vacuum, or the spacing space may be filled with a dielectric material through which the electron beam and the terahertz wave are transmitted well.

Hereinafter, a principle in which the terahertz wave generated from the device of the present invention is formed to have the uniform distribution and linear polarization will be described in more detail with reference to FIG. 4.

As described above, if the electron bundle of the ultra-short wave radiated from the accelerator 130, i.e., the electron beam passes through the thin film 120, the coherent transition radiation that is radially spread around the position is generated. At this time, in the present invention, as illustrated in the front view of FIG. 4, the traveling path of the electron beam is formed so as to meet a center line of the parabola formed by the end surface of the parabolic mirror 115.

As illustrated in the front view of FIG. 4, the coherent transition radiation is spread radially around the position through which the electron beam passes. At this time, as the terahertz wave (part indicated by S in FIG. 4) traveled in an opposite side of the parabolic mirror 115, i.e., upward from the position through which the electron beam passes is spread, an output density thereof is getting weaker and weaker, and therefore in the present invention, the wave corresponding to the part S is not used.

On the other hand, the terahertz wave traveled in a side toward the parabolic mirror 115, i.e., downward from the position through which the electron beam passes is reflected on the parabolic mirror 115 as illustrated in the front view of FIG. 4. At this time, due to the shape characteristic of the parabolic mirror 115, the traveling path of the wave reflected on the parabolic mirror 115 is directed upward. As described above, since the terahertz wave is radially spread around the position through which the electron beam passes, as illustrated in the front view of FIG. 4, all the waves in various directions toward the parabolic mirror 115 are traveled in parallel to each other while being directed upward.

At this time, as illustrated in FIGS. 2 to 4, an upper edge of the thin film 120 is formed in a straight line, and the heights of the plurality of the thin films 120 are formed so as to be sequentially increased or decreased toward the extending direction of the parabolic mirror barrel 110. In particular, it is preferable that the heights of the plurality of thin films 120 are linearly increased or decreased and thus the ends of the thin film 120 form one plane.

When the shape of the thin film 120 is formed as described above, the terahertz waves radiated by being traveled in the respective spacing spaces are coherently combined into a single wavefront at the end of the spacing space and radiated into a free space. That is, the wavefronts of the ultra-short terahertz waves radiated from the edge of the spacing space are combined with each other coherently, and the ultra-short terahertz waves are radiated while maintaining a planar wavefront in the free space. The radiated terahertz wave can be easily focused or transported by using a separate focusing optical system including mirrors, lenses, and the like.

The terahertz wave generated by the above-described method forms and linearly polarized light, and forms collimated waves (except for the diffraction of the terahertz wave) as illustrated in the front view of FIG. 4. In addition, the device for generating a terahertz wave of the present invention generates a wave which has a wavefront formed in a uniform distribution.

The device for generating a terahertz wave of the present invention radiates the coherent radiation in the terahertz spectral region by passing the electron beam through the plurality of thin films, thereby generating a much higher-output terahertz wave than the traditional method for generating a terahertz wave (photoconductive antenna, optical rectification, or the like). In addition, the device for generating a terahertz wave is enough to increase the number of thin films in order to increase the power, and therefore has excellent economical efficiency.

Figure 1:
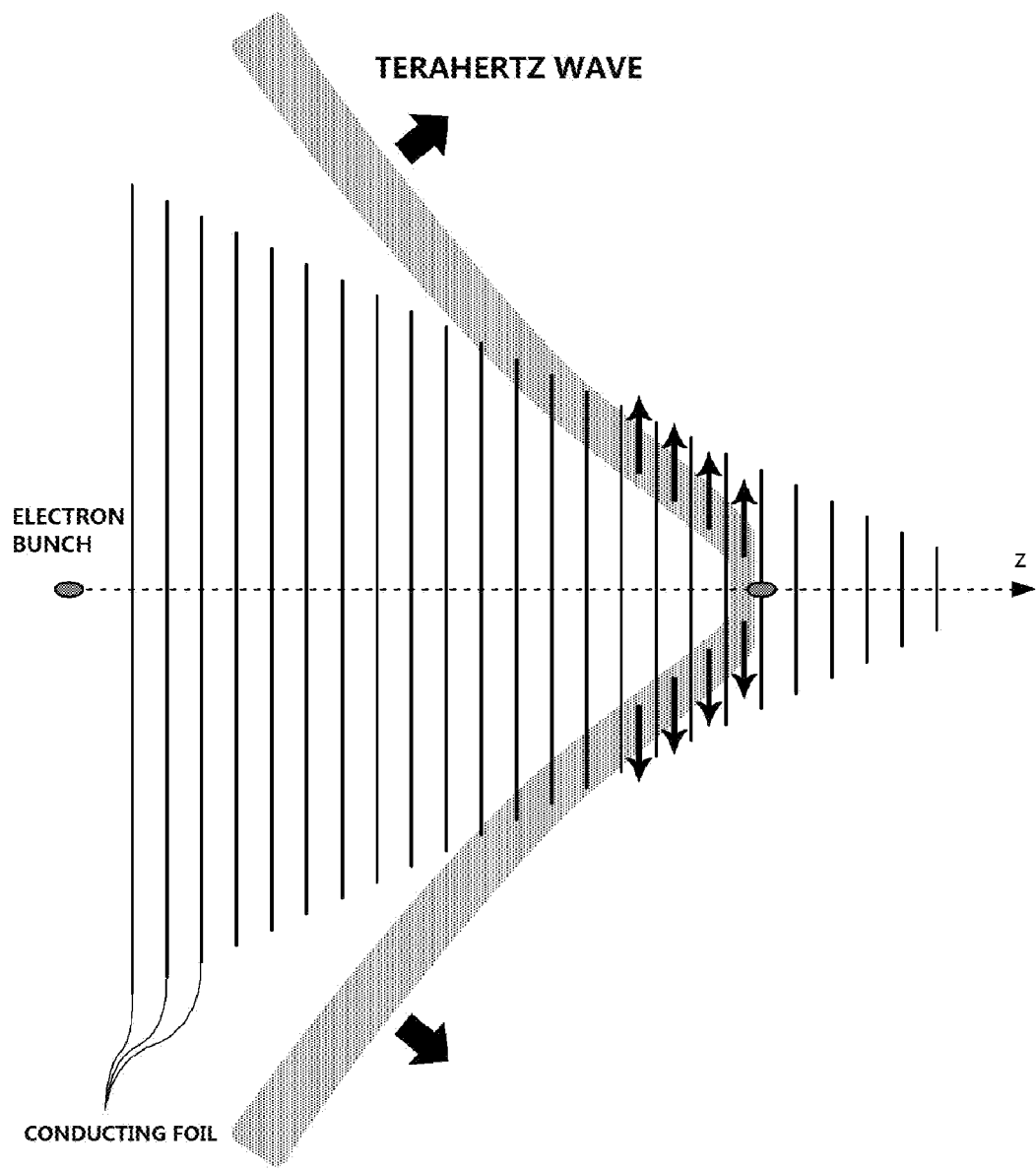
FIG. 1 is a configuration diagram of a device for generating an ultra-short terahertz wave including the existing conical multiple foils.

In addition, as described above, since the device for generating a conical terahertz wave illustrated in FIG. 1 generates the donut-shaped wave having no output at the central part, it is difficult to apply when wanting the uniform distribution or linearly polarized light. However, according to the present invention, since the uniform distribution and the collimated wave of the same linearly polarized light are generated as described above, the device for generating a linearly polarized ultra-short terahertz wave can be widely applied to a wider range than before, and thus industrial utilization thereof is dramatically improved.

The present invention is not limited to the above-mentioned exemplary embodiments but may be variously applied, and may be variously modified by those skilled in the art to which the present invention pertains without departing from the gist of the present invention claimed in the claims.

INDUSTRIAL APPLICABILITY

In other words, according to the present invention, the device for generating a high-power ultra-short terahertz wave can be implemented even in the small-sized apparatus by reducing the capacity and cost of the expensive electron accelerator, and also has excellent characteristics to allow the generated terahertz wave to have the uniform output distribution and linear polarization, such that the device can be used for a greater variety of fields than the related art. In particular, the device for generating a high-output ultra-short terahertz wave is expected to be used in advanced research and security inspection technology.

The invention claimed is:

1. A device for generating a linearly polarized ultra-short terahertz wave, comprising:
   a parabolic mirror barrel configured to extend in one direction, and having a parabolic mirror concaved on an upper surface thereof, with an end surface of the parabolic mirror perpendicular to the extending direction forming a parabola;
   a plurality of thin films configured to be arranged on the parabolic mirror in the extending direction of the parabolic mirror barrel and having at least some areas thereof disposed to overlap each other; and
   an electron accelerator configured to generate an electron beam passing through the plurality of thin films,
   wherein spacing spaces are formed between some areas in which the plurality of thin films overlap each other, and when the electron beam passes through the plurality of thin films and the spacing spaces, a linearly polarized terahertz wave is generated between the spacing spaces.

2. The device for generating a linearly polarized ultra-short terahertz wave of claim 1, wherein when the electron beam passes through the thin films, the electron beam is formed so that the ultra-short terahertz wave is radially wave-guided in a direction perpendicular to the extending direction in the spacing space.

3. The device for generating a linearly polarized ultra-short terahertz wave of claim 2, wherein a traveling path of the electron beam is formed to meet a central line of the parabola formed by the end surface of the parabolic mirror.

4. The device for generating a linearly polarized ultra-short terahertz wave of claim 3, wherein the terahertz wave traveled downward from a position through which the electron beam passes is reflected on the parabolic mirror to be traveled in parallel upward.

5. The device for generating a linearly polarized ultra-short terahertz wave of claim 4, wherein an upper edge of the thin films is formed in a straight line, and
heights of the plurality of thin films are sequentially increased or decreased toward the extending direction.

6. The device for generating a linearly polarized ultra-short terahertz wave of claim 5, wherein the heights of the plurality of thin films are linearly increased or decreased.

7. The device for generating a linearly polarized ultra-short terahertz wave of claim 6, wherein wavefronts of the ultra-short terahertz waves radiated from edges of the spacing spaces are combined with each other, and the ultra-short terahertz waves are radiated while maintaining a planar wavefront in a free space.

8. The device for generating a linearly polarized ultra-short terahertz wave of claim 6, wherein the plurality of thin films are disposed to be parallel with each other so that an interval between the spacing spaces is constant.

9. The device for generating a linearly polarized ultra-short terahertz wave of claim 8, wherein the electron beam travels in a direction perpendicular to the thin films.

10. The device for generating a linearly polarized ultra-short terahertz wave of claim 1, wherein the spacing space is a vacuum or is filled with a dielectric material.

11. The device for generating a linearly polarized ultra-short terahertz wave of claim 1, wherein the thin films are made of a metal material.

12. The device for generating a linearly polarized ultra-short terahertz wave of claim 1, wherein the electron beam is formed in a pulse duration of several picoseconds or less.

* * * * *